(12) United States Patent
Kamihara et al.

(10) Patent No.: US 8,150,645 B2
(45) Date of Patent: Apr. 3, 2012

(54) AUTOMATIC ANALZYER

(75) Inventors: Kumiko Kamihara, Mito (JP);
Tomonori Mimura, Kasama (JP);
Shinichi Fukuzono, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 495 days.

(21) Appl. No.: 12/362,818

(22) Filed: Jan. 30, 2009

(65) Prior Publication Data
US 2009/0198463 A1    Aug. 6, 2009

(30) Foreign Application Priority Data

Jan. 31, 2008    (JP) .................................. 2008-020039

(51) Int. Cl.
*G06F 17/18*    (2006.01)
(52) U.S. Cl. .............. 702/81; 702/179; 702/19; 702/22; 436/10
(58) Field of Classification Search .................... 702/19, 702/22, 81, 179; 436/10, 11, 15, 16, 17, 436/18, 63
See application file for complete search history.

(56) References Cited

U.S. PATENT DOCUMENTS

| | | | |
|---|---|---|---|
| 5,446,681 A * | 8/1995 | Gethner et al. | 702/27 |
| 6,509,192 B1 * | 1/2003 | Young | 436/10 |
| 7,079,986 B2 * | 7/2006 | Sieracki | 702/189 |
| 7,968,832 B2 * | 6/2011 | Okuda et al. | 250/201.3 |
| 2003/0092184 A1 * | 5/2003 | Young | 436/10 |

FOREIGN PATENT DOCUMENTS

| | | |
|---|---|---|
| JP | 6-281656 | 10/1994 |
| JP | 2000-187037 | 7/2000 |
| JP | 2000-266756 | 9/2000 |
| JP | 3420791 | 4/2003 |

OTHER PUBLICATIONS

"A Study for Measurement Uncertainty in Routine Test Using Automatic Analyzer" by Y. Iizuka, et al., vol. 32, No. 1, 2007.
"Uncertainty of Routine Test Values Transmitted From Standard System" by S. Kani., Clinical Chemistry, vol. 36, Supplementary No. 1, pp. 151-153, 2007.

* cited by examiner

*Primary Examiner* — Carol Tsai
(74) *Attorney, Agent, or Firm* — Mattingly & Malur, P.C.

(57) ABSTRACT

Measurement of the uncertainty used for quality control typically involves a plurality of factors. When the uncertainty exceeds a clinical permissible value, time is required for a medical technologist to investigate and to determine the factor causing the uncertainty. It is thus beneficial to automatically investigate factors in complicated uncertainty, particularly from the view point of reagents and samples which are subject to quality change and that are prone to affect the measurement quality. Quality control samples having a plurality of concentration levels are measured to calculate the average, coefficient of variation, standard deviation, and other numerical values. When quality control samples having n (n≧2) different concentration levels are measured, variation patterns determine the factor causing the uncertainty, the factor being specific to each of $3^n$ different combinations of variation patterns.

6 Claims, 5 Drawing Sheets

AUTOMATIC ANALZYER

BACKGROUND OF THE INVENTION

1. Field of the Invention

The present invention relates to an automatic analyzer which performs qualitative and quantitative analyses of a biological sample, such as blood, urine, etc. More particularly, the invention relates to an automatic analyzer which is provided with a quality control function.

2. Description of the Related Art

An automatic analyzer performing qualitative and quantitative analyses of a biological sample, such as blood, urine, and the like, mixes a reagent which reacts with a component under measurement in the sample, and measures reagent color variations and the luminescence of a labeled substance contained in the reagent in order to perform analysis. In this case, measurement values may vary due to aging of the reagent, aging of the optical system including a photometer, a photoelectron multiplier, or the like, and variations in the dispensing quality of dispensing and stirring mechanisms, and the like. Therefore, today's automatic analyzers periodically create a calibration curve by using a known amount of standard sample (calibrator) and check the validity of a measured concentration by using a quality control sample (control substance), thus controlling the measurement quality. These quality control procedures are periodically performed in order to ensure that measurement results of the sample are correct. In routine tests, quality control for clinical testing equipment such as a biochemistry automatic analyzer, or the like is indispensable for stably acquiring exact data without being affected by reagent properties, machine troubles, and the like. Approaches for quality control include internal quality control and external quality control. With internal quality control, measurement value variations are observed for each individual apparatus on a daily basis (individual variation) and in units of several days to several months (day-to-day variation). With external quality control, in order to obtain the same measurement results in every hospital, measurements are performed by using the same standard samples in different inspection institutions for correcting measurement variations among the different inspection institutions.

One quality control method is to evaluate the accuracy of measurements by using standard substances. Specifically, this method performs the steps of:
repetitively performing measurement with a target measuring instrument by using standard substances (quality control samples such as standard liquids or control substances) having a known or constant concentration; and determining the average, the variation range, and the like of measurement values to supervise whether or not the measurement process is stable.

The above-mentioned controlled data is generally represented as a control chart which is a statistical method for setting a quality control limit range statistically obtained and checking whether the measurement process is stable or maintained in a stable state.

When a measurement value controlled in this way exceeds the quality control limit range, it is necessary to investigate the cause and restore the measurement process to the stable state. The above-mentioned measurement value deviation is possibly caused by various factors such as the standard liquids, control substances, or reagents used for measurement, as well as the experimental environment (temperature, humidity, and the like) and facilities or measuring instruments (abnormal temperature of constant-temperature bath, a degraded lamp, or the like in the case of biochemistry analyzers).

Conventional automatic analyzers, on the contrary, perform quality control through the steps of: plotting a control chart; recording information such as the replacement date of reagent, a lamp, or the like in a recording section; and displaying the information in the control chart together with quality control values. In this case, the user visually determines the cause of control value deviation based on the user's experiences. Recent years have seen an international trend of numerical value calibration and certainty check based not on the former quality control techniques but on the uncertainty (parameters accompanying measurement results for characterizing value variation which can rationally be associated with measured quantities). The definition and calculation method of the uncertainty used for quality control have come to be widely known by the establishment of ISO15189 (Medical laboratories—Particular requirements for quality and competence) and the promotion activities of the Japanese Standards Association, and the like. The above-mentioned former techniques are disclosed in JP-A-6-281656, Japanese Patent No. 3420791, JP-A-2000-266756, JP-A-2000-187037, and Non-patent References 1 and 2.

Non-patent Reference 1: Academic Journal of Japanese Association of Clinical Laboratory Automation (JSCLA), Vol. 32, No. 1, pp. 19-25: A Study for Measurement Uncertainty in Routine Test using Automatic Analyzer Non-patent Reference 2: Clinical Chemistry, Vol. 36, Supplementary No. 1, pp. 151-153, 2007: Uncertainty of Routine Test Values Transmitted from Standard System

SUMMARY OF THE INVENTION

Both in the former quality control techniques based on reproducibility and accuracy and in the recently regarded quality control technique based on uncertainty, it is possible to detect a problem in quality control when a numerical value abnormally varies. However, although the uncertainty serves as an index for representing the technical reliability, there is no unified view for in-depth investigation of the cause when the uncertainty exceeds a clinical permissible value, i.e., whether the problem is caused by equipment or reagent. Since measurement of the uncertainty involves many factors such as equipment state, including its maintenance control, reagent, and quality control sample, time-consuming labor is required for an ordinary medical technologist to investigate the factors in the uncertainty. In particular, it is commonly not easy for the technologist to determine the particular factor during a routine clinical test. Therefore, in order to remove the cause, the test must be stopped. This may cause test results to be significantly delayed or may force the medical technologist to proceed with the test without sufficiently maintaining the quality. As mentioned earlier as related art, techniques for maintaining a constant quality and systems for warning of degraded quality have been studied and improved. However, while the investigation of the factor in uncertainty relies on the judgment of the medical technologist, the importance of a unified view or unified judgment system increases when uniformity of the quality and measurement values with respect to outside facilities is required, as well as internal quantity.

In particular, among the factors in uncertainty, reagents are subject to quality change by storage conditions of lots. Therefore, it is difficult to investigate the factor in uncertainty, whether the problem is caused by a quality control sample or measurement reagent. Nevertheless, there has been no choice but to rely on the medical technologists' experiences to determine the factor in uncertainty.

Non-patent Reference 1 describes data uncertainty measurement conducted in recent years, wherein quality control samples having different concentrations are used. According to the measurement, measurement values of medium- and high-concentration quality control samples are stable but data variation of measurement values of low-concentration quality control samples increase. This means the measurement value of a sample with a low existing quantity of a target measurement item may not be accurate during measurement of an actual patient body even if the results of measurement with quality control samples having a single concentration fall within a permissible variation range.

An object of the present invention is to provide an automatic analyzer provided with a function for automatically determining the factor in such complicated uncertainty without relying on a medical technologists' judgment, and to provide a related analysis method.

In order to attain the above-mentioned object, the automatic analyzer according to the present invention includes a detection unit 101, a storage unit 102, a calculation unit 103, a display unit 104, an operation unit 105, and a determination unit 106, as shown in FIG. 1. The storage unit 102 such as a hard disk stores measurement data output from the detection unit 101 of the automatic analyzer, and stores and updates concentrations and types of standard liquids and control substances at a plurality of levels. The calculation unit 103 calculates the concentration, standard deviation, coefficient of variation, date, time, and the like for each measurement from the output measurement data. The display unit 104, in conjunction with the storage unit 102 for storing and updating calculated data, displays control charts and numerical values. The operation unit 105, including a keyboard, CRT, or the like, sets a judgment value (boundary value for determining whether or not measured values are abnormal) and types and concentrations of samples. The determination unit, including a logic having a plurality of branch points to compare a calculated numerical value with a judgment value, determines whether or not an abnormal condition occurs and the cause thereof. The result of judgment output from the determination unit 106 is displayed on the display unit 104 and an alarm is generated.

The automatic analyzer uses quality control samples having a plurality of concentration levels for quality control to calculate the average, coefficient of variation, standard deviation, and the like of measurement values. Numerical value variations can be classified into three different variation patterns: falling, stable, and rising patterns. Therefore, when quality control samples having n (n≧2) different concentration levels are measured, the automatic analyzer presumes the factor in uncertainty specific to each of $3^n$ different combinations of variation patterns.

When a measurement value deviates from a quality control range, the automatic analyzer in accordance with the present invention, investigates the cause of the deviation thus remarkably saving labor and time consumed to recover a state where normal values can be measured. This makes it possible to reduce the load to, and to reduce possible artificial judgment mistakes made by the medical technologist, thus avoiding a judgment error due to individual difference. Further, since the automatic analyzer accumulates data in the storage unit and analyzes how an interval or what cause tends to make a measurement value deviate from the quality control limit range occur, it is expected that quality deviation can be prevented in advance.

DESCRIPTION OF THE PREFERRED EMBODIMENTS

Embodiments of the present invention will be explained below with reference to the accompanying drawings.

First Embodiment

Figure 1:
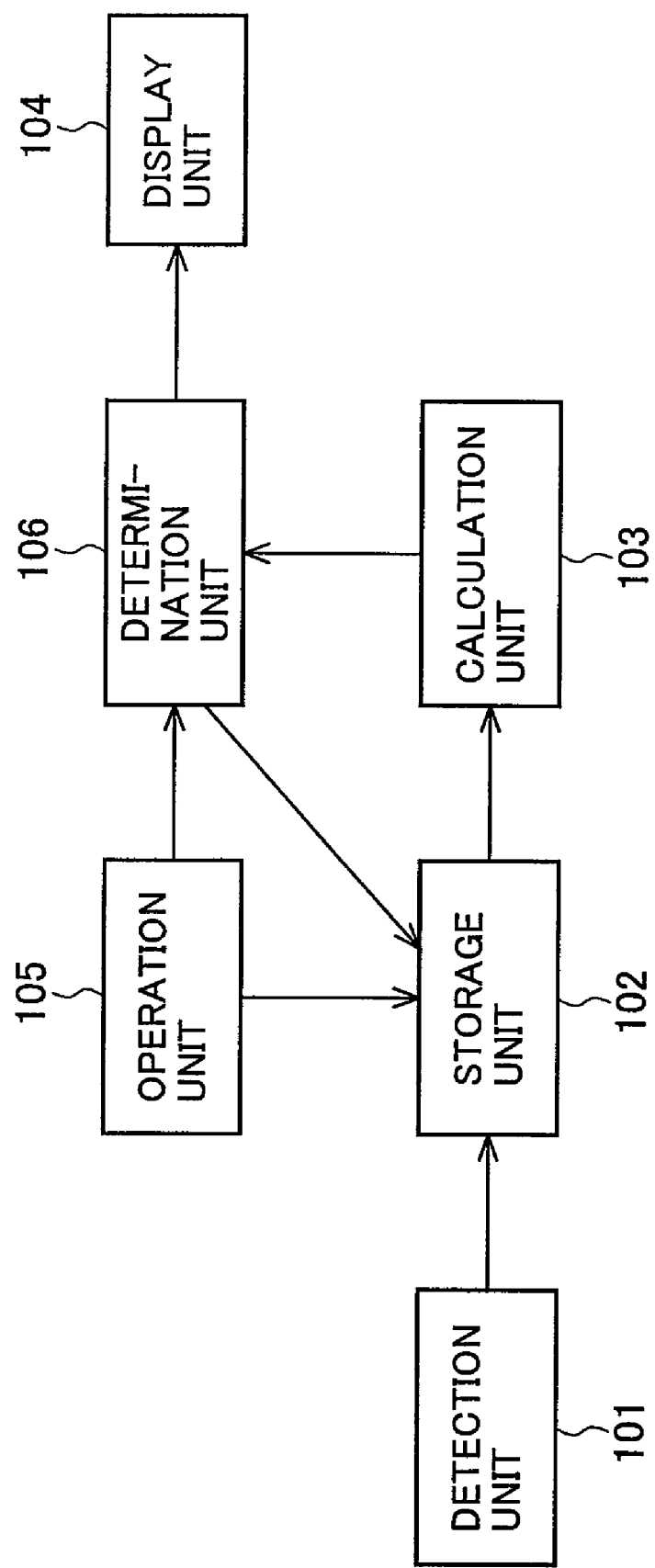
FIG. 1 is a block diagram showing an overview configuration of an automatic analyzer according to the present invention.

FIG. 1 is the best mode of the automatic analyzer according to the present invention.

In order to perform quality control, the automatic analyzer inputs directly or through a barcode reader the information on a plurality of quality control samples and information on measurement items, and then starts measurement. This measurement can be implemented in various ways: before or after starting a test every day, at intervals of a predetermined number of samples during tests, and at a predetermined time. Measurement data output from the detection unit 101 is stored in computer memory, and then read by the calculation unit 103 to calculate the average, measurement range, standard deviation, coefficient of variation, and the like. The calculated numerical values can be accumulated in the storage unit 102 and then integrated with previously measured data to create a control chart. Then, the determination unit 106 compares numerical values calculated by the calculation unit with a judgment value input from the operation unit 105 to determine whether or not numerical value variations occur, as well as the cause of variations. The determination unit is provided with the information required for judgment. The factor obtained by the judgment can be displayed on the display unit 104 or can be notified as an alarm.

Figure 2:
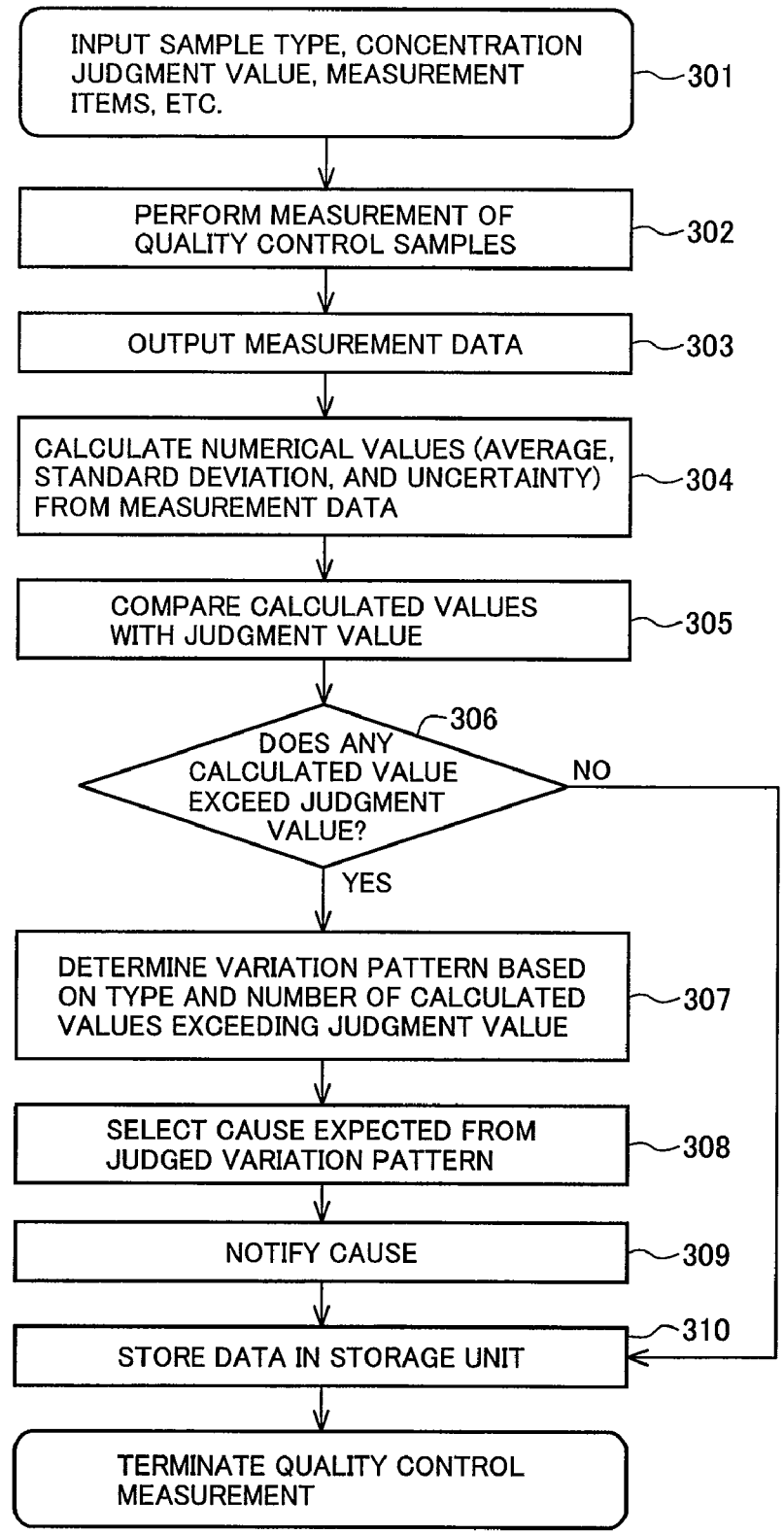
FIG. 2 is a flow chart of processing from measurement of a quality control sample to judgment of cause of variation.

FIG. 2 is a flow chart showing a logic from quality control measurement to judgment.

In Step 301, names and types of reagents to be used, measurement items, user-defined judgment value, and the like are set and stored by operation from the operation unit such as the keyboard, CRT, or the like connected to the computer. In Step 302, the automatic analyzer measures the registered quality control samples. The automatic analyzer, after calibration is completed every day, measures the quality control samples before, during, or after measurement of a patient body or a plurality of times. In Step 303, the detection unit outputs the obtained measurement data to the computer. In Step 304, the computer calculates the average, standard deviation, and the like based on the received data. In Step 305, the determination unit compares values obtained by calculation with the judgment value previously input or a default judgment value. In step 306, as a result of the comparison, the determination unit determines if there are any samples for which the calculated value exceeds the judgment value for each item. When the calculated value does not exceed the judgment value, the determination unit determines that the certainty is maintained and stores the data in the storage unit in Step 310. When the calculated value exceeds the judgment value, the determination unit determines variation patterns, such as, for example, types and number of variations for each item in Step 307, and then selects the factor in uncertainty presumed from the judged variation patterns in Step 308. In Step 309, the judged factor and control chart are displayed on the display unit together with items and other data. When this measurement is performed during tests, the display screen may not be selected and therefore it may be desirable to generate an alarm. Then, in Step 310, the obtained data is accumulated in the storage unit such as a database. Accuracy control is performed according to the above-mentioned flow.

1. Quality Control Samples

Although any types of standard serums, pool serums, and control substances containing more than a certain quantity of substances of measurement items can be used for uncertainty measurement, quality control samples having a plurality of concentration levels are prepared for each measurement item. It is necessary that the concentration levels be within the measurement range of the reagents and equipment used. Samples having three different concentration levels are used in the present embodiment. It is particularly preferable to use three levels with certain intervals, for example, a low level (hereinafter referred to as L), a middle level (hereinafter referred to as M), and a high level (hereinafter referred to as H). L denotes the vicinity of a lower limit of the reference range of the normal measurement value; M denotes the vicinity of an upper limit of the reference range thereof; and H denotes a level which is at least twice the normal measurement value.

2. Measurement Items

Although any measurement items that can be measured with the automatic analyzer can be used, it is desirable that each item can be measured with both the enzyme method and immunization. More than about 300 measurement items are known. Main items include total protein (TP), albumin (ALB), lactate dehydrogenase (LD), aspartate aminotransferase (AST), alanine aminotransferase (ALT), alkaline phosphatase (ALP), amylase (AMY), pancreatic amylase (P-AMY), leucine aminopeptidase (LAP), γ-glutamyl transpeptidase (γGT), cholinesterase (CHE), creatine kinase (CK), total cholesterol (T-Cho), neutral fat (TG), HDL-cholesterol (HDL-C), LDL-cholesterol (LDL-C), free fatty acid (FEA), urea nitrogen (UN), creatinine (CRE), uric acid (UA), glucose (Glu), hemoglobin A1C (HbA1c), lactic acid (LA), pyruvic acid (PA), total bilirubin (T-BIL), direct bilirubin (D-BIL), calcium (Ca), sodium (Na), inorganic phosphorus (IP), serum iron (Fe), unsaturated iron binding capacity (UIBC), creatine kinase MB (CK-MB), phospholipid (PL), C reactive protein (CRP), rheumatoid cause (RF), immunoglobulin G (IgG), immunoglobulin A (IgA), immunoglobulin M (IgM), complement 3 (C3), complement 4 (C4), antistreptolysin-O (ASO), etc. In particular, uric acid (UA), aspartate aminotransferase (AST), alanine aminotransferase (ALT), creatinine (CRE), γ-glutamyl transpeptidase (γGT), etc. are known for the dispersion tendency of low-concentration regions, and therefore it is more desirable to apply these measurement items to the present invention.

3. Measurement Data Calculation Procedures

Figure 3:
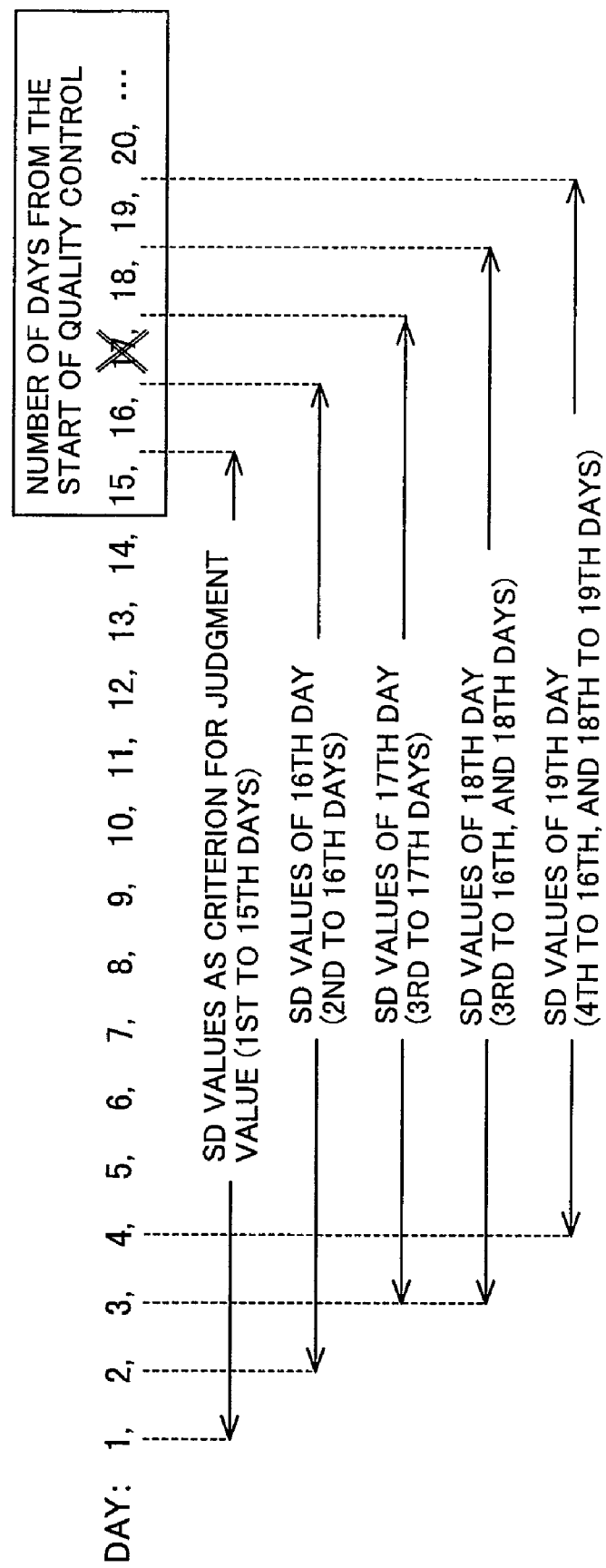
FIG. 3 is an exemplary method for calculating SD values used for routine quality control.

Data variation can be measured by measuring the same sample a plurality of times. Actually, in measurement of the simultaneous repeatability of reagents, independent data for 20 to 30 measurements are used. Also, in individual or day-to-day quality control, although the availability of more data items for more number of measurements provides higher quality, measurement is possible with data for at least two measurements. Since at least 15 independent measurement values is recommended for presuming the uncertainty in ordinary quality control, measurement procedures using data of 15 times measurement will be described for the present embodiment. Average, standard deviation, and the like can be used for quality measurement. For example, FIG. 3 shows quality control based on SD values by using data for 15 measurements as the parent population. The data for 15 days from the first day on which measurement is started is used to accumulate quality control data and to calculate SD values used as a judgment value. For each quality control sample, the same sample is measured a plurality of times and then the average is used as the measurement value of the day. In order to equalize the reference values used for judgment and parent population of measurement values subjected to comparison, the data for the past 15 days including the measurement date is used. However, when any of these measurement values of three different concentration level samples exceeds a judgment value, the data for the relevant day is not used since it affects subsequent SD values. For example, when data obtained on the 17th day exceeds a judgment value, SD values of the next day (18th day) are calculated based on the data of 15 days excluding the 17th day, i.e., the third to 16th days and the 18th day. Likewise, on the 19th day, SD values are calculated based on the data for 15 days, i.e., the fourth to 16th days and the 18th to 19th days. When quality control measurement is performed several times a day, it is desirable to calculate SD values based on the data for the past 15 measurements.

4. Judgment Value Setup Procedures

It is very rare that the same measurement values and the same SD values are obtained every day. Since numerical values will vary even slightly, it is important to determine whether or not the variation is within an ordinary data spread range, not to determine whether or not SD value variation occurs.

The most basic and most commonly used quality control limit range uses a value twice or three times the variation (standard deviation). Hereinafter, this value is referred to as the σ value. When the distribution of variation is 1σ, 2σ, and 3σ of the normal distribution, 68%, 95%, and 99% of data fall within the quality control limit, respectively. In actual measurement, a more severe quality control limit increases the possibility that even a value variation not due to abnormal cause may be out of the quality control limit range, thereby disturbing ordinary test procedures. Since quality requirements differ for each institution and measurement item, the medical technologist can arbitrarily set a judgment value. The judgment value can be input or changed before or after measurement of quality control samples.

In order to set a pertinent judgment value, collection of preliminary data is required. When the measurement process is in a stable state, different types of standard serums having a constant concentration are measured n times every day, and data is continuously accumulated for K days. It is desirable that the same quality control samples and reagents are used during this period. The average, standard deviation, coefficient of variation, and the like are calculated based on the accumulated data. These values are multiplied by X, or Z % is added to or subtracted from them to derive a judgment value.

The judgment value can be fixed or variable. It can be made variable by increasing the parent population each time quality measurement is performed.

In the present embodiment, the same item is measured five times and an average is calculated in each of the first 15 days. Then, the standard deviation for the 15 days is calculated and the $2\sigma$ (SD×2) value is set as a judgment value.

5. Display Method

Figure 4:
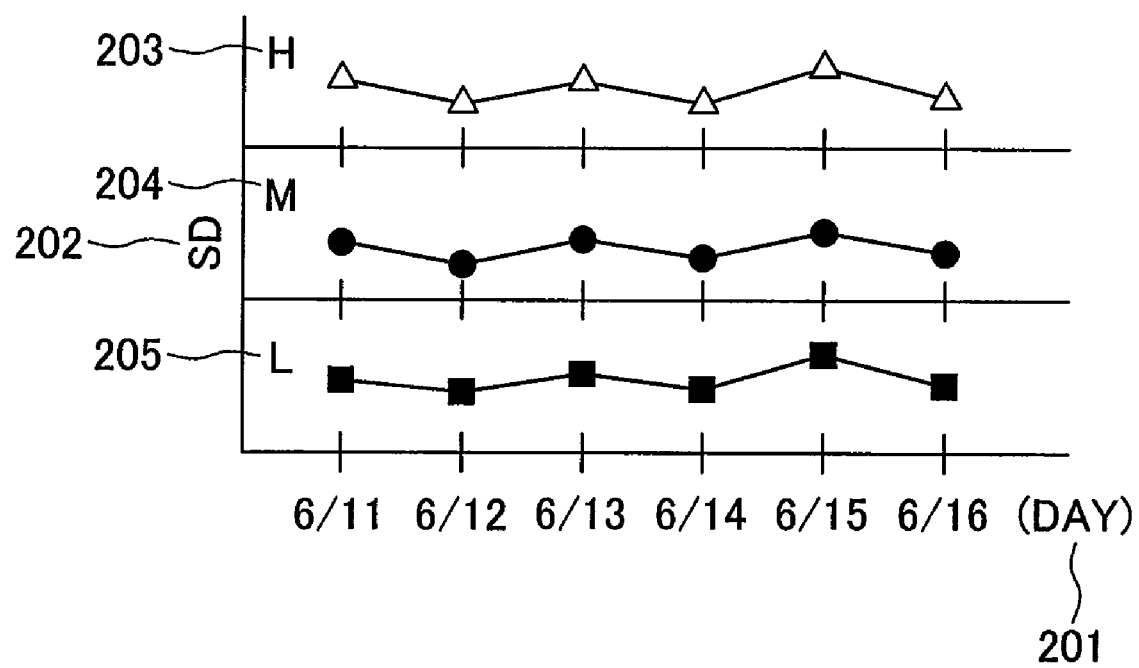
FIG. 4 is an example of a quality control chart.

It is also possible to display measured or calculated data in numerical form. As the control chart method for quality control, it is possible to use known techniques, for example, X-R control chart method, X bar-R control chart method, X bar-Rs-R control chart method, twin plot method, plus-minus control chart method, multirule control chart method, cumulative sum control chart method, scatter chart method, and the like. For example, for facilitating the viewing of measurement value variations, it is more desirable to create a control chart having a horizontal axis assigned the measurement date and a vertical axis assigned the normalized value not affected by the concentration of quality control samples, such as CV value, SD value, and the like. FIG. 4 is a general control chart having a horizontal axis 201 assigned the measurement date and a vertical axis 202 assigned the SD value. Control charts can be displayed independently for each concentration and, more preferably, a plurality of control charts can be overlapped or arranged on the same screen. For example, in FIG. 4, control charts for a high-concentration level sample (H) 203, a medium-concentration level sample (M) 204, and a low-concentration level sample (L) 205 are vertically arranged.

When control charts for each concentration are arranged or overlapped, although calculated numerical values such as average, SD value, etc. can be displayed according to the original Y-axis scale, it is more desirable to display the numerical values with a fixed scale regardless of numerical value for each concentration, for example, so as to fit into the span between specified upper- and lower-limit control values, thereby making it easier to compare variations for each concentration with each other.

In FIG. 4, the horizontal axis is assigned the date for a fixed time period in units of week, month, and year (for example, 30 days), and updated on a daily basis. Further, control charts for a plurality of items specified by the user can be displayed on the same screen.

6. Judgment Method

In routine measurements, when each measurement value is compared with a target value, three different variation patterns are considered, that is, the value remains unchanged, decreases, and increases. Therefore, in the case where n different quality control samples are measured, $3^n$ (n-th power of 3) different combinations of variation patterns are considered. Specifically, when quality control is performed by using three different quality control samples, the number of combinations of variation patterns is 27 ($3^3$). In calculation of the average, for example, these 27 different combinations must be examined. However, since the measurement range, SD value, CV value, and the like, increase with increasing data variation, a decrease in these values means a decrease in variation. In quality control with biochemistry analyzers, therefore, a decrease in the SD value is not regarded as a problem but regarded as the same meaning as no variation, that is, maintained stability. Accordingly, an increase in the SD value means that the stability of the measurement process is not maintained, raising a problem which must be noticed. As for SD value variation, therefore, only two different variation patterns may be considered: whether the SD value increases or not. Thus, when n ($n \geqq 2$) different quality control samples are used, $2^n$ (n-th power of 2) different combinations of variation patterns may be considered.

Figure 5A:
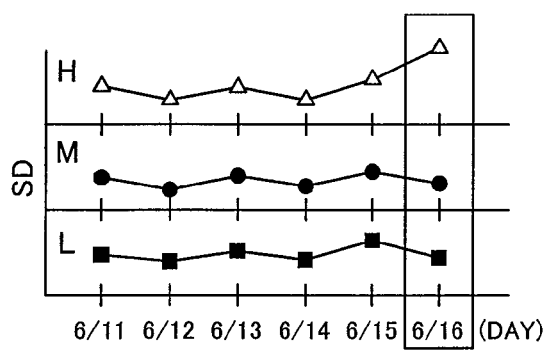
FIGS. 5A to 5G show variation patterns of quality control samples shown in the control chart, FIG. 5A.
showing SD value when only H abnormally increases, FIG. 5B showing SD value when only M abnormally increases, FIG. 5C showing SD value when only L abnormally increases, FIG. 5D showing SD values when H and M abnormally increase, FIG. 5E showing SD values when M and L abnormally increase, FIG. 5F showing SD values when H and L abnormally increase, FIG. 5G showing SD values when H, M, and L abnormally increase.
Figure 5B:
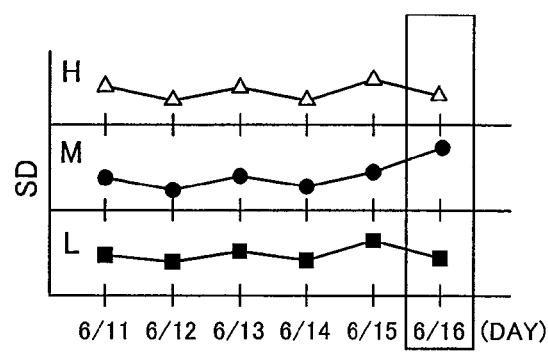
Figure 5C:
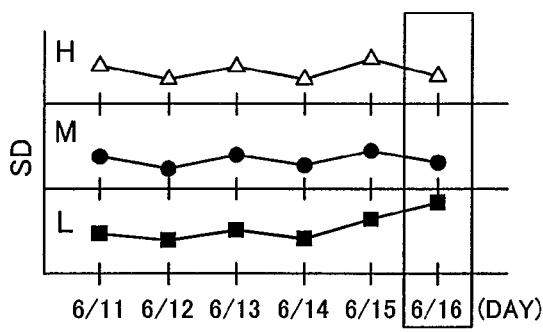
Figure 5D:
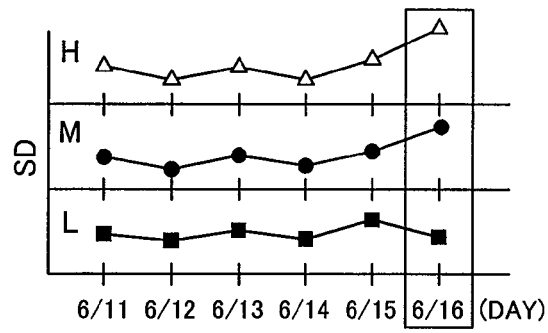
Figure 5E:
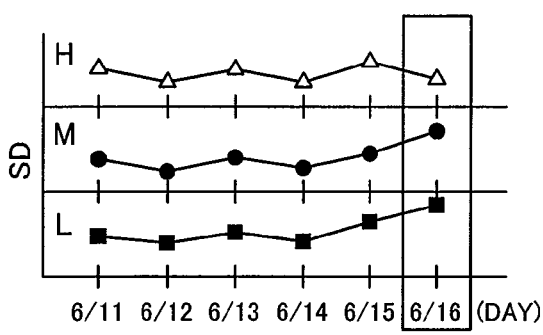
Figure 5F:
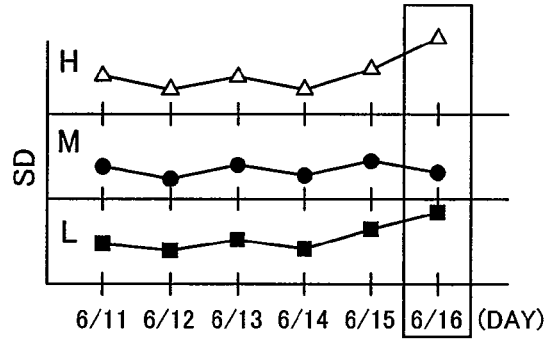
Figure 5G:
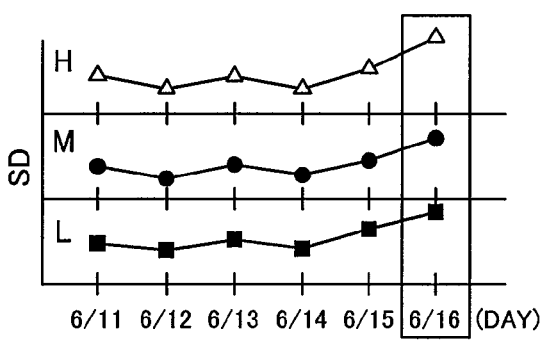

In the present embodiment, since quality control samples having three different concentration levels are measured, the number of combinations of variation patterns of the SD values is ($2^3$). However, since a state where the SD value remains unchanged (or changes very slightly) in three different-level concentration samples means that normal measurement can be achieved, seven (8−1) different combinations of variation patterns of the SD value are used to indicate the factor in uncertainty. These seven different combinations of variation patterns are shown in FIGS. 5A to 5G. When data variation on the date enclosed by a frame (June 16) is noticed in FIGS. 5A to 5G, there are three different combinations of variation patterns in which one of three values abnormally increases: increase only in H (FIG. 5A), increase only in M (FIG. 5B), and increase only in L (FIG. 5C). There are three different combinations of variation patterns in which two out of three values abnormally increase: increase in H and M (FIG. 5D), increase in M and L (FIG. 5E), and increase in H and L (FIG. 5F). Then, there is a case where, in all of H, M, and L, SD values abnormally increase (FIG. 5G).

The factors of these seven different combinations of variation patterns will be considered below. In the case where an abnormal increase is in one of three values (FIGS. 5A, 5B, and 5C), when the peculiarity is specific not to a measurement item but to a quality control sample having the relevant concentration, there is a high possibility that the quality control sample may have been degraded or defective.

In the case where, in the H and M levels, out of the three concentration level samples, the SD values abnormally increase (FIG. 5D), while the quality of values in a low-concentration sample which is liable to cause data spread is maintained, the values in the medium-concentration sample and in the high-concentration sample are abnormal. In this case, degradation of the measurement reagent is estimated since absence of linearity in the reagent is considered.

In the case where, in the M and L levels, out of the three concentration level samples, the SD values abnormally increase (FIG. 5E), since values in a high-concentration sample are not affected but incorrect measurement values arise with the use of medium- and low-concentration samples, there is a high possibility that the quality control sample may have been degraded. Depending on the measurement item, the effect caused by the concentration arises. For example, in the case of uric acid (UA), when ammonia in the air is captured into the quality control sample, the concentration of ammonia in the sample is likely to change. Further, since a standard liquid having a lower concentration generally provides more unstable quality, it is presumed that a quality control sample having a lower concentration provides a shorter usable life even if three different quality control samples are opened on the same date.

In the case where, in the H and L levels, out of the three concentration level samples, the SD values abnormally increase (FIG. 5F), since the measurement values of a medium-concentration sample are stable, the inclination of the calibration curve measured before the test is assumed to be fluctuating centering on medium-concentration values. Therefore, it is presumed that the calibration curve of relevant date may not have been correctly drawn.

In the case where, in all of the three concentration level samples, SD values abnormally increase (FIG. 5G), when the increase is specific to a measurement item, the cause is a degraded reagent for the measurement item. When values in all measurement items abnormally increase, the cause may not be the reagent but may be the lamp, the temperature of the constant-temperature bath, and other mechanical factors.

From these considerations, the cause of variation can be determined by classifying variation patterns into the above-mentioned seven different combinations of variation patterns for quality control samples having three different concentrations.

Sample Judgment (1)

Calculation-based presumption of the cause of day-to-day variation by noticing the SD value will be explained below. A judgment value is set for each quality control sample. The medical technologist can optimally set the value with the setup screen. For example, when the SD value calculated on the 15th day from the start of measurement is used as a reference value, a numerical value (2SD), or twice the SD value, is set as the judgment value. In routine measurement, when the data is stable as shown in Table 1, the SD values of H, M, and L do not exceed the judgment value.

TABLE 1

Relation between variation patterns of quality control samples and transition of SD values

| SD value | Judgment value (example) | Stable | \multicolumn{7}{c}{Variation patterns of quality control samples having three different concentrations} |
|---|---|---|---|---|---|---|---|---|---|
|  |  |  | a | b | c | d | e | f | g |
| H | <2SD (H) | (Within limit) | over |  |  | over |  | over | over |
| M | <2SD (M) | (Within limit) |  | over |  | over | over |  | over |
| L | <2SD (L) | (Within limit) |  |  | over |  | over | over | over |

In pattern a, the SD value of H exceeds the judgment value. In pattern b, the SD value of M exceeds the judgment value. In pattern c, the SD value of L exceeds the judgment value. In pattern d, the SD values of H and M exceed the reference range. In pattern e, the SD values of M and L exceed the reference range. In pattern f, the SD values of H and L exceed the reference range. Further, in pattern g, the SD values of H, M, and L exceed the reference range. As mentioned above, the types and number of quality control samples exceeding the judgment value differ for each variation pattern. Pattern recognition when the SD value is exceeded is performed using the judgment value.

Calculations for this pattern recognition are automatically performed each time a quality control sample is measured, and a judged cause is displayed on the screen showing the quality control together with the control chart.

If pattern recognition can be automatically performed, it is possible to display the judged cause, together with an alarm, with reference to the judgment list shown in Table 2.

TABLE 2

Judgment list of possible causes

| Pattern | State of control chart | Detailed Description | Possible cause |
|---|---|---|---|
| a | One of three SD values increases. | Only H (high concentration) | Degraded quality control substance H |
| b |  | Only M (medium concentration) | Degraded quality control substance M |
| c |  | Only L (low concentration) | Degraded quality control substance L |
| d | Two out of three SD values increase. | H and M | Degraded measurement reagent |
| e |  | M and L | Degraded quality control substance |
| f |  | H and L | Incorrect calibration curve |
| g | Three SD values increase. | Specific to item | Degraded measurement reagent |
|  |  | All items | Mechanical factor (lamp, temperature, etc.) |

Sample Judgment (2)

Results of sample measurement are displayed as a control chart. The control chart provides a line of the judgment value for each of H, M, and L, facilitating the visual recognition of a case where the three different quality control samples have variations correlating each other. The pattern of the control chart shown in FIG. 5 is overlapped with the obtained control chart on the same screen, and the medical technologist visually judges pattern matching. The medical technologist clicks or checks the control chart having the same pattern on the screen to indicate the result of judgment based on a correspondence table like Table 2. Checking completes the registration of judgment results.

What is claimed is:

1. An automatic analyzer comprising:
   storage means for storing measurement results of quality control samples each having a plurality of known concentrations which plurality of known concentrations are different from each other;
   calculation means for calculating at least one of an average, coefficient of variation, and standard deviation, of the plurality of measurement results stored in said storage means;
   classification means for classifying the at least one of the average, coefficient of variation, and standard deviation, calculated by said calculation means in each of the measurement results in each of the plurality of known concentrations of the measured quality control samples; and
   registration means for registering combinations of variation patterns of said measurement results of each of said plurality of known concentrations of said quality control samples of the at least one of the average, coefficient of variation, and standard deviation, as classified by said classification means.

2. The automatic analyzer according to claim 1, wherein the automatic analyzer includes means for associating a cause of a measurement uncertainty with each of the combinations of variation patterns registered by said registration means.

3. The automatic analyzer according to claim 1, wherein, when a measurement result of one of the quality control samples fails to match any of the combinations of variation patterns registered by the registration means, the automatic analyzer registers the non-matching measurement result in said registration means as a new variation pattern.

4. The automatic analyzer according to claim 1, further including a communication line and wherein at least one of said calculation means, classification means, and registration means is included in a host computer which is connected with the automatic analyzer through the communication line.

5. The automatic analyzer according to claim 2, wherein the automatic analyzer includes setup means for setting a judgment value for judging the cause of a measurement uncertainty.

6. The automatic analyzer according to claim 2, wherein the automatic analyzer includes display means for displaying the at least one of the average, coefficient of variation, and standard deviation of the quality control sample as well as the related cause of the measurement uncertainty.

* * * * *